US007417043B2

(12) United States Patent
Sonesson et al.

(10) Patent No.: US 7,417,043 B2
(45) Date of Patent: Aug. 26, 2008

(54) MODULATORS OF DOPAMINE NEUROTRANSMISSION

(75) Inventors: Clas Sonesson, Billdal (SE); Bengt Andersson, deceased, late of Göteborg (SE); by Ingela Marianne Svan, legal representative, Göteborg (SE); by Anders Kristoffer Lilja, legal representative, Göteborg (SE); by Liselott Lilja Rönnqvist, legal representative, Göteborg (SE); by Jenny Maria Carlberg, legal representative, Årsta (SE); Susanna Waters, Göteborg (SE); Nicholas Waters, Göteborg (SE); Joakim Tedroff, Danderyd (SE)

(73) Assignee: NeuroSearch Sweden AB, Göteborg (SE)

(*) Notice: Subject to any disclaimer, the term of this patent is extended or adjusted under 35 U.S.C. 154(b) by 0 days.

(21) Appl. No.: 11/016,967

(22) Filed: Dec. 21, 2004

(65) Prior Publication Data
US 2006/0135531 A1   Jun. 22, 2006

Related U.S. Application Data

(62) Division of application No. 10/168,173, filed as application No. PCT/SE00/02674 on Dec. 22, 2000, now Pat. No. 6,903,120.

(30) Foreign Application Priority Data
Dec. 22, 1999 (SE) .................................... 9904724

(51) Int. Cl.
C07D 295/06 (2006.01)
A01N 43/60 (2006.01)

(52) U.S. Cl. .................. 514/247; 544/394; 544/392; 544/395; 424/250

(58) Field of Classification Search ................. 546/192; 514/317, 247; 544/224, 336, 394, 395, 392; 424/250
See application file for complete search history.

(56) References Cited

U.S. PATENT DOCUMENTS

| 3,326,916 A | 6/1967 | Creighton |
| 3,539,573 A | 11/1970 | Schmutz et al. |
| 4,202,898 A | 5/1980 | Depoortere |
| 4,267,328 A * | 5/1981 | Najer et al. ................. 544/394 |
| 4,333,942 A | 6/1982 | Eistetter et al. |
| 4,415,736 A | 11/1983 | Ciganek et al. |
| 4,504,660 A | 3/1985 | Klaubert et al. |
| 4,892,875 A | 1/1990 | Meguro et al. |
| 5,462,947 A | 10/1995 | Svensson et al. |
| 5,502,050 A | 3/1996 | Gross |
| 6,175,015 B1 | 1/2001 | Yuan et al. |
| 6,903,120 B2 * | 6/2005 | Sonesson et al. ............ 514/331 |
| 6,924,374 B2 * | 8/2005 | Sonesson et al. ............ 546/192 |

FOREIGN PATENT DOCUMENTS

| EP | 0 060 179 | 2/1982 |
| EP | 2 083 476 A | 3/1982 |
| EP | 0094159 | 11/1983 |
| EP | 0 369 887 | 5/1990 |
| EP | 0 533 267 | 9/1992 |
| EP | 0 533 266 A1 | 3/1993 |
| EP | 0 533 268 A1 | 3/1993 |
| EP | 0 675 118 B1 | 10/2002 |
| FR | 1459013 | 11/1966 |
| GB | 850662 | 10/1960 |
| GB | 1 560 271 | 2/1980 |
| GB | 2 027 703 | 2/1980 |
| GB | 2 078 746 A | 1/1982 |
| NL | 6510107 | 2/1966 |
| WO | WO 89/05799 | 6/1989 |
| WO | WO 91/09594 | 7/1991 |
| WO | WO 92/18475 | 10/1992 |
| WO | WO 93/00313 | 1/1993 |
| WO | WO/9703986 | 2/1997 |
| WO | WO 98/11068 | 3/1998 |

(Continued)

OTHER PUBLICATIONS

Chemical Abstract CA 132:35590. "Synthesis of piperidine analogos of 1-(3-chlorophenyl)piperazine, a well known serotonin ligand." Radl et al., Journal of Heterocyclic Chemistry (1999), 36(4), pp. 1017-1022.

(Continued)

Primary Examiner—James O. Wilson
Assistant Examiner—Paul V. Ward
(74) Attorney, Agent, or Firm—Buchanan Ingersoll & Rooney PC

(57) ABSTRACT

A 3-substituted 4-(phenyl-N-alkyl)-piperazine compound of the following formula:

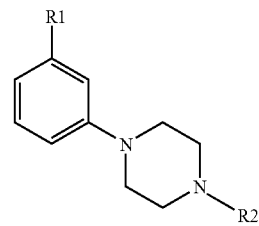

wherein $R_1$ is selected from the group consisting of $OSO_2CF_3$, $OSO_2CH_3$, $SO_2R_3$, $COCF_3$, $COCH_3$ and $COCH_2CH_3$, wherein $R_3$ is as defined hereafter; $R_2$ is selected from the group consisting of $C_1$-$C_4$ alkyls, allyl, $CH_2CH_2CH_2F$, $CH_2CF_3$, 3,3,3-trifluoropropyl and 4,4,4-trifluorobutyl; $R_3$ is selected from the group consisting of $C_1$-$C_3$ alkyls, $CF_3$, and $N(CH_3)_2$; with the proviso that when $R_1$ is $SO_2R_3$ and $R_3$ is a $C_1$-$C_3$ alkyl, then $R_2$ is not $CH_2CH_2OCH_3$; or a pharmaceutically acceptable salt thereof are provided. Also, pharmaceutical compositions comprising the above compound and methods wherein the above compound is used for the treatment of various disorders are provided.

8 Claims, No Drawings

FOREIGN PATENT DOCUMENTS

| WO | WO 00/03713 | 1/2000 |
| --- | --- | --- |
| WO | WO 00/78728 | 12/2000 |
| WO | WO01/46145 A1 * | 6/2001 |
| WO | WO 01/46146 A1 | 6/2001 |
| WO | WO 02/05819 A1 | 1/2002 |
| WO | WO 02/059108 A1 | 8/2002 |
| WO | WO 2004/099150 A2 | 11/2004 |
| WO | WO 2005/019215 A1 | 3/2005 |
| WO | WO 2005/121092 A1 | 12/2005 |

OTHER PUBLICATIONS

Chemical Abstract CA 116:250000. "Quantitative structure-metabolism relationship analyses of MAO-medicated toxication of 1-methyl-4-phenyl-1,2,3,5-tetrahydropyridine and analogs." Cosimo et al., Chemical Research in Toxicology (1992), 5(3), pp. 366-375.

Chemical Abstract DN 65:38471, also cited as NL 6510107.

U.S. Appl. No. 10/168,297, filed Nov. 20, 2002.

Joseph T. Coyle et al, Science vol. 219, 1184-1190 (1983).

Grunblatt et al. (PubMed Abstract 10335493).

Grunblatte et al. (PubMed Abstract 10863545).

Carlsson et al., "Interactions Between Glutamatergic and Monoaminergic Systems within the Basal Ganglia—Implications for Schizophrenia and Parkinson's Disease", TINS, (1990), pp. 272-276, vol. 13, No. 7, Elsevier Science Publishers Ltd., United Kingdom.

Feldman et al. (Editors), "Principles of Neuropsychopharmacology", Chapter 17—Mind Altering Drugs, (1997), pp. 731, 762, 763, Sinauer Associates, Inc., Publishers, Sunderland, Massachusetts, USA.

Bloom et al. (Editors), "Psychopharmacology—The Fourth Generation of Progress", Chapter 21, pp. 227, 237, Chapter 22, pp. 245, 254, Chapter 25, pp. 283, 292, Chapter 26, pp. 295-301, Chapter 6, pp. 759-760, 1725, 744-746, Chapter 68, pp. 787, 793-795, Chapter 80, pp. 921-925, 927-928, Chapter 101, pp. 1205, 1207-1209, Chapter 111, pp. 1311, 1317, 1318, 1320, Chapter 126, pp. 1479-1482, Chapter 137, pp. 1591, 1600, Chapter 138, pp. 1609-1610, 1612, (1995), Raven Press, New York, New York, USA.

Clas Sonesson et al., "Substituted (S)-Phenylpiperidines and Rigid Congeners as Preferential Dopamine Autoreceptor Antagonists: Synthesis and Structure-Activity Relationships", Journal of Medicinal Chemistry, 1994, vol. 37, No. 17, pp. 2735 to 2753.

Zhang, et al., "Studies on antimalarials. III. Synthesis and antimalarial effects of some derivatives of 2,4-diamino-6-substituted piperazinylquinazolines", Acta Pharmaceutica Sinica, Jun. 1981, pp. 415-424, vol. 16, No. 6, Shanghai Inst. Pharm. Ind. Res., Shanghai, Peop, Rep. of China.

Takai, et al., "Reaction of Spiro[4H-3,1-benzoxazine-4,4'-piperdin]-2(1H)-one Derivatives and Related Compounds with Phosphorus Oxychloride", Chemical & Pharmaceutical Bulletin., May 1986, pp. 1901-1906, vol. 34, No. 5, Pharmaceutical Society of Japan, Tokyo, JP.

Egawa, et al., "A New Synthesis of 7H-Pyrido[1,2,3-de][1,4]benzoxazine Derivatives Including an Antibacterial Agent, Ofloxacin[1]", Chemical & Pharmaceutical Bulletin, Oct. 1986, pp. 4098-4102, vol. 34, No. 10, Pharmaceutical Society of Japan, Tokyo, JP.

Beugelmans, et al., "Synthèsse d'hétérocycles à 5 et 6 chaînons par une stratégie combinant des réactions $S_NAr$ et $S_{RN}1$", Bull Soc Chim Fr., 1995, pp. 306-313, vol. 132, Elsevier, Paris, FR.

Morita, et al., "Practical Application of the Palladium-catalyzed Amination in Phenylpiperazine Synthesis: An Efficient Synthesis of a Metabolite of the Antipsychotic Agent Aripiprazole", Tetrahedron, May 7, 1998, pp. 4811-4818, vol. 54, No. 19, Pergamon, Elsevier Science Ltd., Oxford, England & NY, USA.

Smaill, et al., "Mono- and difunctional nitrogen mustadr analogues of the DNA minor groove binder pibenzimol. Synthesis, cytotxicity and interaction with DNA", Anti-Cancer Drug Design, 1998, pp. 221-242, vol. 13, Oxford University Press.

Klaubert, et al., "N-(Aminophenyl)oxamic Acids and Esters a Potent, Orally Active Antiallergy Agent", J. Med. Chem., 1981, p. 742-748, vol. 24, American Chemical Society, Washington, DC.

Self, et al., "cine and tele Substitutions in the Reaction of 2,3-Dinitroaniline with Secondary Amines", J.C.S. Chem. Comm., 1980, pp. 281-282, Royal Society of Chemistry, UK.

Elslager, et al., "Folate Antagonists. 3. 2,4-Diamino-6-(heterocyclic)quinazolines, a Novel Class of Antimetabolites with Potent Antimalarial and Antibacterial Activity", Journal of Medicinal Chemistry, 1972, pp. 827-836, vol. 15, No. 8, American Chemical Society, Washington, DC.

Berberian, et al., "Comparison of Schistosomicidal Activity of Xanthenones adn 4-Methyl-3-chloroanilines and Their Hydroxymethyl Analogs in Swiss Mice and Syrian Hamsters Infected with Schistosoma mansoni", Jpurnal of Medicinal Chemistry, Jul. 1969, pp. 607-610, vol. 12, No. 4, American Chemical Society, Washington, DC.

Henry, "A Facile Synthesis of Piperazines from Primary Amines (1)", Journal of Heterocyclic Chemistry, 1966, pp. 503-511, vol. 3, No. 4, Heterocorporation, USA.

Oshiro, et al., "Novel Antisychotic Agents with Dopamine Autoreceptor Agonist Properties: Synthesis and Pharmacology of 7-[4-(4-Phenyl-1-piperazinyl)butoxy]-3,4-dihydro-2(1H)-quinolinone Derivatives", J. Med. Chem., 1998, pp. 658-667, vol. 41, American Chemical Society, Washington, DC.

Manoury, et al., "Synthesis and Analgesic Activities of Some (4-Substituted phenyl-1-piperazinyl)alkyl 2-Aminobenzoates and 2-Aminocotinates", Journal of Medicinal Chemistry, 1979, pp. 554-559, vol. 22, No. 5, American Chemical Society, Washington, DC.

"Biologic Test Methods", Burger's Medicinal Chemistry, Fourth Edition, Part III, Edited by Manfred E. Wolff, pp. 872-873, John Wiley & Sons, NY, USa.

Strange, "Antipsychotic Drugs: Importance of Dopamine Receptors for Mechanisms of Therapeutic Actions and Side Effects", Pharmacologic Reviews, 2001, pp. 119-133, vol. 53, No. 1, The American Society for Pharmacology and Experimental Therapeutics, USA.

Wieslaw Gessner et al., "Synthesis and Dihydropteridine Reductase Inhibitory Effects of Potential Metabolites of the Neurotoxin - methyl-4-phenyl-1,2,3,6-tetrahydropyridine" Journal of Medicinal Chemistry, American Chemical Society, vol. 28, No. 3, 1985, pp. 311-317.

Journal Chem. Society, Bergel et al. 1944, pp. 261 to 264. Beilstein Registry No. 183878 and 206256, Bielstein Institute for Organic Chemostry, Franfurt0Main, Germany.

V. Nacci et al. "Antiblastic Substances. LII. Tylophorine Analogs.1. Synthesis and Cytostiic and Cytoxic Activity of 4-(3,4-dimethoxyphenyl)piperdine", Farmaco, Edizione Scientifica, vol. 328, No. 5, 1973, pp. 399-419.

English Translation of Jul. 12, 2006 Korean Offical Action issued in counterpart Korean Application No. 2005-7024520.

Mar. 22, 2004 Search Report issued in European counterpart Application No. 1 419 773.

* cited by examiner

MODULATORS OF DOPAMINE NEUROTRANSMISSION

This is a Divisional Patent Application of U.S. patent application Ser. No. 10/168,173, filed Nov. 21, 2002 now U.S. Pat. No. 6,903,120, which is a 35 U.S.C. § 371 filing of International Application No. PCT/SE00/02674, filed Dec. 22, 2000, and claims priority under 35 U.S.C. § 119(a)-(d) for the filing of Swedish Application No. 9904724-3, filed Dec. 22, 1999.

FIELD OF THE INVENTION

The present invention relates to new modulators of dopamine neurotransmission, and more specifically to new substituted 4-(phenyl N-alkyl)-piperazines and 4-(phenyl N-alkyl)-piperidines, and use thereof.

BACKGROUND OF THE INVENTION

Dopamine is a neurotransmitter in the brain. Since this discovery, made in the 1950s, the function of dopamine in the brain has been intensely explored. To date, it is well established that dopamine is essential in several aspects of brain function including motor, cognitive, sensory, emotional and autonomous (e.g. regulation of appetite, body temperature, sleep) functions. Thus, modulation of dopaminergic function may be beneficial in the treatment of a wide range of disorders affecting brain functions. In fact, both neurologic and psychiatric disorders are treated with medications based on interactions with dopamine systems and dopamine receptors in the brain.

Drugs that act, directly or indirectly, at central dopamine receptors are commonly used in the treatment of neurologic and psychiatric disorders, e.g. Parkinson's disease and schizophrenia. Currently available dopaminergic pharmaceuticals have severe side effects, such as extrapyramidal side effects and tardive dyskinesia in dopaminergic antagonists used as antipsychotic agents, and dyskinesias and psychoses in dopaminergic agonists used as anti-Parkinson's agents. Therapeutic effects are unsatisfactory in many respects. To improve efficacy and reduce side effects of dopaminergic pharmaceuticals, novel dopamine receptor ligands with selectivity at specific dopamine receptor subtypes or regional selectivity are sought for. In this context, also partial dopamine receptor agonists, i.e. dopamine receptor ligands with some but not full intrinsic activity at dopamine receptors, are being developed to achieve an optimal degree of stimulation at dopamine receptors, avoiding excessive dopamine receptor blockade or excessive stimulation.

Compounds belonging to the class of substituted 4-(phenyl-N-alkyl)-piperazine and substituted 4-(phenyl-N-alkyl)-piperidines have been previously reported. Among these compounds, some are inactive in the CNS, some display serotonergic or mixed serotonergic/dopaminergic pharmacological profiles while some are full or partial dopamine receptor agonists or antagonists with high affinity for dopamine receptors.

A number of 4-phenylpiperazines and 4-phenylpiperidine derivatives are known and described, for example Costall et al. European J. Pharm. 31, 94, (1975), Mewshaw et al. Bioorg. Med. Chem. Lett., 8, 295, (1998). The reported compounds are substituted 4-phenylpiperazine's, most of them being 2-, 3- or 4-OH phenyl substituted and displaying DA autoreceptor agonist properties.

Fuller R. W. et al, J. Pharmacol. Exp. Therapeut. 218, 636, (1981) disclose substituted piperazines (e.g. 1-(m-trifluoromethylphenyl)piperazine) which reportedly act as serotonin agonists and inhibit serotonin uptake. Fuller R. W. et al, Res. Commun. Chem. Pathol. Pharmacol. 17, 551, (1977) disclose the comparative effects on the 3,4-dihydroxy-phenylacetic acid and Res. Commun. Chem. Pathol. Pharmacol. 29, 201, (1980) disclose the comparative effects on the 5-hydroxyindole acetic acid concentration in rat brain by 1-(p-chlorophenol)-piperazine.

Boissier J. et al Chem Abstr. 61:10691c, disclose disubstituted piperazines. The compounds are reportedly adrenolytics, antihypertensives, potentiators of barbiturates, and depressants of the central nervous system.

A number of different substituted piperazines have been published as ligands at $5-HT_{1A}$ receptors, for example Glennon R. A. et al J. Med. Chem., 31, 1968, (1988), van Steen B. J., J. Med. Chem., 36, 2751, (1993), Mokrosz, J. et al, Arch. Pharm. (Weinheim) 328, 143-148 (1995), and Dukat M.-L., J. Med. Chem., 39, 4017, (1996). Glennon R. A. discloses, in international patent applications WO 93/00313 and WO 91/09594 various amines, among them substituted piperazines, as sigma receptor ligands. Clinical studies investigating the properties of sigma receptor ligands in schizophrenic patients have not generated evidence of antipsychotic activity, or activity in any other CNS disorder. Two of the most extensively studied selective sigma receptor antagonists, BW234U (rimcazole) and BMY14802, have both failed in clinical studies in schizophrenic patients (Borison et al, 1991, Psychopharmacol Bull 27 (2): 103-106; Gewirtz et al, 1994, Neuropsycho-pharmacology 10:37-40).

Further, WO 93/04684 and GB 2027703 also describe specific substituted piperazines useful in the treatment of CNS disorders.

SUMMARY OF THE INVENTION

The object of the present invention is to provide new pharmaceutically active compounds, especially useful in treatment of disorders in the central nervous system, which do not have the disadvantages of the above described substances.

In the work leading to the present invention, it was found that it is desired to provide substances with specific pharmacological properties, namely substances that have modulating effects on dopamine neurotransmission. These properties have not been described earlier, and they are not possible to obtain with the earlier known compounds. The compounds according to the present invention have a very surprising and interesting dualistic dopaminergic action profile with antagonist-like effects on brain neurochemistry and mild agonist-like effects on normal behavior, but they induce inhibition of behavior in states of hyperactivity.

The present invention thus relates to new 3-substituted 4-(phenyl-N-alkyl) piperazines and 3-substituted 4-(phenyl-N-alkyl) piperidines in the form of free base or pharmaceutically acceptable salts thereof, pharmaceutical compositions containing said compounds and use of said compounds in therapy.

One subject of the invention is to provide new compounds for therapeutic use, and more precisely compounds for modulation of dopaminergic systems in the mammalian brain, including human brain.

Another subject of the invention is to provide compounds with therapeutic effects after oral administration.

More precisely, the present invention relates to 3-substituted 4-(phenyl N-alkyl)-piperazine and 4-(phenyl-N-alkyl)-piperidine compounds of Formula 1:

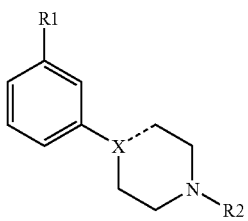

(1)

and pharmaceutically acceptable salts thereof, wherein:

X is selected from the group consisting of N, CH, and C, however X may only be C when the compound comprises a double bond at the dotted line;

$R_1$ is selected from the group consisting of $OSO_2CF_3$, $OSO_2CH_3$, $SOR_3$, $SO_2R_3$, $COR_3$, $NO_2$, and $CONHR_3$, wherein $R_3$ is as defined below, and when X is CH or C $R_1$ may also be selected from the group consisting of $CF_3$, CN, F, Cl, Br, and I;

$R_2$ is selected from the group consisting of $C_1$-$C_4$ alkyls, allyls, $CH_2SCH_3$, $CH_2CH_2OCH_3$, $CH_2CH_2CH_2F$, $CH_2CF_3$, 3,3,3-trifluoropropyl, 4,4,4-trifluorobutyl, and —$(CH_2)$—$R_4$, wherein $R_4$ is as defined below;

$R_3$ is selected from the group consisting of $C_1$-$C_3$ alkyls, $CF_3$, and $N(R_2)_2$, wherein $R_2$ is as defined above;

$R_4$ is selected from the group consisting of $C_3$-$C_6$ cycloalkyls, 2-tetrahydrofurane and 3-tetra-hydrofurane.

The compounds according to the present invention possess dopamine-modulating properties and are useful in treating numerous central nervous system disorders including both psychiatric and neurological symptoms.

Diseases in which compounds with modulating effects on dopaminergic systems may be beneficial are in disorders related to ageing, for preventing bradykinesia and depression and for the improvement of mental functions. They may also be used to improve cognitive functions and related emotional disturbances in neurodegenerative and developmental disorders as well as after brain damage.

The compounds according to the invention can be used to improve all symptoms of psychosis, including schizophrenia and schizophreniform disorders as well as drug induced psychotic disorders. The compounds according to the invention may also be used in behavioral disorders usually first diagnosed in infancy, childhood, or adolescence as well as in impulse control disorders. Also, speech disorders such as stuttering may improve. They may also be used for treating substance abuse disorders as well as disorders characterized by misuse of food.

Mood and anxiety disorders, personality disorders, and conversion hysteria may also be treated with the compounds according to the invention.

Neurological indications include the treatment of Huntington's disease and other movement disorders as well as movement disorders induced by drugs. Restless legs and related disorders as well as narcolepsy may also be treated with compounds included according to the invention. They may also improve mental and motor function in Parkinson's disease, and in related parkinsonian syndromes. They may also be used to ameliorate tremor of different origins. They may be used in the treatment of headaches and used to improve brain function following vascular or traumatic brain injury. Moreover, they may be used to relieve pain in conditions characterized by increased muscle tone.

The compounds according to the present invention have unexpectedly been found to act specifically on dopaminergic systems in the brain. They have effects on biochemical indices in the brain with the characteristic features of selective dopamine antagonists, e.g. producing increases in concentrations of dopamine metabolites.

Yet, dopamine receptor antagonists characteristically suppress behavioral activity and induce catalepsy, while the compounds of this invention show no, or only limited, inhibitory effects on spontaneous locomotion. In contrast they may induce a slight behavioral activation with concomitant increases in small-scale movements, e.g. stops in the center of the behavior recording arena, similar to that induced by dopaminergic agonists. The behavioral activation is limited, not reaching the profound increases in activity induced by direct or indirect dopaminergic agonists. On the other hand, the preferred substances reduce the increase in activity induced by direct or indirect dopaminergic agonists, i.e. d-amphetamine and congeners.

Thus, the compounds of this invention surprisingly show an interesting dualistic dopaminergic action profile with antagonist like effects on brain neurochemistry and mild agonist like effects on normal behavior, but inhibition of behavior in states of hyperactivity. The action profile suggests modulatory effects on dopaminergic functions, clearly different from known compounds belonging to these chemical classes or effects anticipated of typical dopamine receptor antagonists or agonists from these or other chemical classes.

Given the involvement of dopamine in a large variety of CNS functions and the clinical shortcomings of presently available pharmaceuticals acting on dopamine systems, the novel class of dopaminergic modulators presented in this invention may prove superior to presently known dopaminergic compounds in the treatment of several disorders related to dysfunctions of the CNS, in terms of efficacy as well as side effects.

Some compounds according to the invention have been found to have surprisingly good pharmacokinetic properties including high oral bioavailability. They are thus suitable for the preparation of orally administered pharmaceuticals. There is no guidance in the prior art how to obtain compounds with this effect on dopamine systems in the brain.

DETAILED DESCRIPTION OF THE INVENTION

Pharmacology

Evidence is available that neurotransmission in the CNS is disturbed in psychiatric and neurologic diseases. In many instances, for example in schizophrenia or Parkinson's disease, pharmacotherapies based on antagonism or agonism at dopamine receptors are useful, but not optimal. In recent years much efforts have been put on finding novel and selective ligands for dopamine receptor subtypes ($D_1$, $D_2$, $D_3$, $D_4$, $D_5$) with the aim to improve efficacy and reduce side effects.

The present invention offers another principle for novel therapeutics based on interactions with dopamine systems. The compounds according to the invention have effects on brain neurochemistry similar to antagonists at dopamine $D_2$ receptors. In contrast to currently used dopamine receptor antagonists the compounds according to the invention show no or limited inhibitory effects on spontaneous locomotion. They may induce behavioral activation with concomitant increases in small-scale movements, e.g. stops in the center of the behavior recording arena, similar to that induced by dopaminergic agonists. The behavioral activation is limited, not reaching the profound increases in activity induced by direct or indirect dopamine receptor agonists. Surprisingly, the preferred substances can actually reduce the increase in activity induced by direct or indirect dopaminergic agonists, i.e. d-amphetamine and congeners.

The preferred structures are substituted in the meta position on the aromatic ring. An example of such a compound is methanesulfonic acid 3-(1-propyl-piperidin-4-yl)-phenyl ester, which is shown in Example 14 below. In rat, this compound increases 3,4-dihydroxyphenylacetic acid in the striatum from 1265±74 (controls) to 3208±236 ng/g tissue at 50 μmol/kg s.c. in combination with a slight increase in behavioral activity; 1485±328 cm/30 min (controls) to 2126±240 cm/30 min at 50 μmol/kg s.c., n=4. Another preferred example of a compound according to the invention is 4-(3-methanesulfonyl-phenyl)-1-propyl-piperidine, further illustrated in Example 6. In rat, this compound increases 3,4-dihydroxy-phenylacetic acid in the striatum from 914±19 (controls) to 1703±19 ng/g tissue at 50 μmol/kg s.c. This increase in dopamine turnover is followed by a trend towards an increase in motor activity from 2030±299 cm/60 min to 2879±398 cm/60 min p=0.14. In animals habituated to the motilitymeter box the compound described in Example 6, 4-(3-methanesulfonyl-phenyl)-1-propyl-piperidine, increases behavioral activity from 476±279 cm/60 min (controls) to 1243±72 cm/60 min, p<0.05, n=4, and 4-dihydroxyphenylacetic acid in the striatum from 975±23 (controls) to 2074±144 ng/g tissue at 50 μmol/kg s.c., p<0.05, n=4.

In addition, the compound described in Example 6, 4-(3-methanesulfonyl-phenyl)-1-propyl-piperidine, has the preferred ability to reduce behavioral activation induced by both d-amphetamine (1.5 mg/kg s.c.) and dizolcipine (Mk-801, 0,7 mg/kg i.p.). d-Amphetamine hyperactivity is reduced from 10694±2165 cm/60 min to 1839±344 cm/60 min, p<0.05 n=4, at 50 μmol/kg s.c. of the compound described in Example 6 and behavioral activation induced by dizolcipine (Mk-801) is reduced from 32580±4303 cm/60 min to 18197±1389 cm/60 min p<0.05, at 50 μmol/kg sc. Surprisingly, the compound described in Example 6 has an oral availability (F) of 85% in rat.

Unlike the somewhat similar compounds described in WO91/09594, the compound of Example 6, 4-(3-methanesulfonyl-phenyl)-1-propyl-piperidine, lacks affinity at the sigma receptor, <50% inhibition of [$^3$H]-DTG binding (according to a method for measurement of sigma binding described by Shirayama Y. et al., 1993, Eur. J. Pharmacol. 237, p 117) at 10 μmol/L to rat brain membranes.

In order to demonstrate the surprising effects of the compounds according to the invention, some of the compounds have been compared to similar compounds according to prior art. The compounds used for comparison with the compounds according to the invention in the comparative examples are thus not compounds according to the invention since they do not exhibit the desired properties.

COMPARATIVE EXAMPLE 1

4-(4-methanesulphonyl-phenyl)-1-propyl piperidine illustrates that substitution in the para position yields inactive compounds. 4-(4-methanesulphonyl-phenyl)-1-propyl piperidine has no effect on 3,4-dihydroxyphenyl-acetic acid in the striatum as demonstrated in the neurochemical experiment; 988±70 (controls) ng/g tissue and 928±51 ng/g tissue at 50 μmol/kg s.c. 4-(4-methanesulphonyl-phenyl)-1-propyl piperidine does not have the properties desired according to the invention.

COMPARATIVE EXAMPLE 2

To further illustrate the importance of the substitition on the aromatic ring for the desired properties, 4-phenyl-1-propyl-piperidine is demonstrated to lack activity in the behavioral assay in the non-pre-treated rat, 3661±494 cm/60 min, controls, to 2553±471 cm/60 min, p>0.05, n=4, at 33 μmol/kg and lacks effects on 3,4-dihydroxyphenyl-acetic acid in the striatum as demonstrated in the neurochemical experiment; 1027±31 (controls) ng/g tissue and 1190±70 ng/g tissue at 33 μmol/kg s.c., p>0.05., 4-phenyl-1-propyl-piperidine] also lacks the desired inhibition of behavioral activity in the d-amphetamine stimulated (17295±4738 cm/60 min, d-amphetamine, to 13764±2919 cm/60 min, n=4, p>>0.05 at 33 μmol/kg.

COMPARATIVE EXAMPLE 3

Further, 1-phenyl-4-propyl-piperazine, described as sigma receptor binding compound in WO91/09594, is found to reduce behavioral activity in the non-pre-treated animal, from 3370±227, controls, to 1923±204 cm/60 min, n=4, p<0.05 at 33 μmol/kg s.c., thus lacking the properties sought for.

COMPARATIVE EXAMPLE 4

Substitution in the ortho position as exemplified by 1-(2-methoxy-phenyl)-4-propyl piperazine yields a compound which increases 3,4-dihydroxyphenylacetic acid in the striatum from 1028±9 (controls) ng/g tissue to 3836±65 ng/g tissue at 50 μmol/kg s.c., p<0.05, n=4. This is followed by the behavioral inhibition not sought for in the present invention; 1651±300 cm/60 min (controls) to 67±34 cm/60 min, at 50 μmol/kg s.c., p<0.05, n=4.

COMPARATIVE EXAMPLE 5

The properties of the substituent in the meta position are important. 1-propyl-4-(3-triflouro-methyl-phenyl) piperazine increases 3,4-dihydroxyphenyl-acetic acid in the striatum from 1066±46 (controls) ng/g tissue to 3358±162 ng/g tissue at 50 μmol/kg s.c., p<0.05, n=4, however, followed by behavioral inhibition from 1244±341 cm/60 min (controls) to 271±137 at 50 μmol/kg s.c., p<0.05, n=4, thus, lacking the properties sought for in the present invention.

COMPARATIVE EXAMPLE 6

Further, the compound of 3-(4-Propyl-piperazine-1-yl)-benzonitrile increases 3,4-dihydroxyphenyl-acetic acid in the striatum from 1432±57 (controls) ng/g tissue to 4498±243 ng/g tissue at 100 μmol/kg s.c., p<0.05, n=4, and reduces 5-hydroxyindole acetic acid from 630±16 (controls) ng/g tissue to 484±26 ng/g tissue at 100 μmol/kg s.c., p<0.05, n=4. These effects are followed by behavioral inhibition from 3959±688 cm/60 min (controls) to 634±266 at 100 μmol/kg s.c., p<0.05, n=4, thus, lacking the properties sought for in the present invention. 3-(4-Propyl-piperazine-1-yl)-benzonitrile has the following properties: m.p. 159° C. (fumarate) MS m/z (relative intensity, 70 eV) 229 (M+, 28), 200 (bp), 157 (27), 129 (22), 70 (25).

COMPARATIVE EXAMPLE 7

Another example of the importance of the substituent is preparation 14 which has no effect on 3,4-dihydroxy-phenyl-acetic acid in the striatum; 1121±36 (controls) ng/g tissue to 1169±42 ng/g tissue at 50 μmol/kg s.c.

COMPARATIVE EXAMPLE 8

The physicochemical properties of the substituent on the basic nitrogen is also important for the desired profile. It is not possible to use any substituent, which is exemplified by 1-phenethyl-4-(3-trifluoromethyl-phenyl)-piperazine described as a sigma receptor ligand in WO 91/09594 and WO 93/00313 which has some effects on 3,4-dihydroxyphenylacetic acid in the striatum; 852±33 (controls) to 1406±77 ng/g tissue at 50 μmol/kg s.c., p<0.05, n=4, but also reduces both 5-hydroxyindoleacetic acid in the striatum from 358±20 (controls) to 289±16 ng/g tissue at 50 mol/kg s.c., p<0.05, n=4, and serotonin (5-HT) from 379±10 (controls) to 282±6 ng/g tissue at 50 μmol/kg s.c., p<0.05, n=4, which is an undesired property according to this invention but in accordance with the reported IC50 of 20,3 nM at the 5-HT$_{1A}$ receptor (WO 93/00313).

COMPARATIVE EXAMPLE 9

In addition, 1-benzyl-4-(3-methanesulfonyl-phenyl)-piperidine and 3-(1-benzyl-piperidin-4-yl)-phenol, compounds with benzylic substitution on the basic nitrogen, both has the undesired property to interact with serotonin systems in the brain. 1-Benzyl-4-(3-methanesulfonyl-phenyl)-piperidine increases 5-hydroxyindoleacetic acid in the striatum from 428±20 (controls) to 487±7 ng/g tissue at 50 μmol/kg s.c., p<0.05, n=4, and reduces serotonin (5-HT) from 442±15 (controls) to 345±18 ng/g tissue at 50 μmol/kg s.c., p<0.05, n=4, and induces the serotonin behavioral syndrome (serotonin behavioral syndrome is e.g. described by Tricklebank et al., 1985, Eur. J. Pharmacol, 106, pp 271-282). 3-(1-Benzyl-piperidin-4-yl)-phenol has the undesired ability to increse 5-hydroxyindoleacetic acid in the striatum from 404±10 (controls) to 492±26 ng/g tissue at 50 μmol/kg s.c., p<0.05, n=4, and reduces serotonin in the limbic region (5-HT) from 734±8 (controls) to 677±20 ng/g tissue at 50 μmol/kg s.c., p<0.05, n=4.

COMPARATIVE EXAMPLE 10

Substitution on the basic nitrogen according to 2-[4-(3-methanesulfonyl-phenyl)piperazin-1-yl]-ethanol] (described in GB 2027703) renders compounds which are inactive in the behavioral activity test; 3238±1089 cm/60 min (controls) to 3782±962 cm/60 min at 33 μmol/kg s.c., n=4, p>0.05, as well as in the neurochemical test; effects on 3,4-dihydroxyphenylacetic acid in the striatum; 1158±126 (controls) to 1239±162 ng/g tissue at 33 μmol/kg s.c., n=4, p>0.05.

The compounds according to the invention are especially suitable for treatment of disorders in the central nervous system, and particularly for treatment of dopamine mediated disorders. They may, e.g. used to ameliorate symptoms of mood disorders, in obesitas as an anorectic agent and in other eating disorders, to improve cognitive functions and related emotional disturbances, to improve cognitive and motor dysfunctions associated with developmental disorders, to improve all symptoms of schizophrenia and schizophreniform disorders as well as other psychoses, to improve ongoing-symptoms as well as to prevent the occurrence of new psychotic episodes, to regulate pathological disorders due to intake of food, coffee, tea, tobacco, alcohol, addictive drugs etc.

The compounds according to the invention can thus be used to treat symptoms in e.g.:

schizophrenia and other psychotic disorders, such as catatonic, disorganized, paranoid, residual or differentiated schizophrenia; schizophreniform disorder; schizo-affective disorder; delusional disorder; brief psychotic disorder; shared psychotic disorder; psychotic disorder due to a general medical condition with delusions and/or hallucinations;

mood disorders, such as depressive disorders, e.g., dysthymic disorder or major depressive disorder; bipolar disorders, e.g., bipolar I disorder, bipolar II disorder, and cyclothymic disorder; mood disorder due to a general medical condition with depressive, and/or manic features; and substance-induced mood disorder;

anxiety disorders, such as acute stress disorder, agoraphobia without history of panic disorder, anxiety disorder due to general medical condition, generalized anxiety disorder, obsessive-compulsive disorder, panic disorder with agoraphobia, panic disorder without agoraphobia, posttraumatic stress disorder, specific phobia, social phobia, and substance-induced anxiety disorder;

eating disorders, such as anorexia nervosa, bulimia nervosa, and obesitas;

sleep disorders, such as dyssomnias, e.g., breathing-related sleep disorder, circadian rhythm sleep disorder, hypersomnia, insomnia, narcolepsy, and "jet lag";

impulse-control disorders not elsewhere classified, such as intermittent explosive disorder, kleptomania, pathological gambling, pyromania, and trichotillomania;

personality disorders, such as paranoid, schizoid or schizotypal disorder; antisocial, borderline, histrionic, and narcissistic disorder; and avoidant, dependent, obsessive-compulsive disorder;

medication-induced movement disorders, such as neuroleptic induced parkinsonism, neuroleptic malignant syndrome, neuroleptic induced acute and tardive dystonia, neuroleptic induced akathisia, neuroleptic induced tardive dyskinesia, medication induced tremor, and medication induced dyskinesias;

substance-related disorders, such as abuse, dependence, anxiety disorder, intoxication, intoxication delirium, psychotic disorder, psychotic disorder with delusions, mood disorder, persisting amnestic disorder, persisting dementia, persisting perception disorder, sexual dysfunction, sleep disorder, withdrawal, and withdrawal delirium due to use ore misuse of alcohol, amphetamine (or amphetamine-like substances), caffeine, cannabis, cocaine, hallucinogens, inhalants, nicotine, opioids, phencyclidine (or phencyclidine-like substances), sedative substances, hypnotic substances, and/or anxiolytic substances;

disorders usually first diagnosed in infancy, childhood, or adolescence, such as mental retardation; learning disorders; motor skills disorders, e.g. developmental coordination disorder; communication disorders, e.g. expressive language disorder, phonological disorder, receptive-expressive language disorder and stuttering; pervasive developmental disorders, e.g. Asperger's disorder, autistic disorder, childhood disintegrative disorder, and Rett's disorder; attention-deficit and disruptive behavior disorders, e.g. attention-deficit/hyperactivity disorder, conduct disorder, and oppositional defiant disorder; feeding and eating disorders of infancy or early childhood, e.g. feeding disorder of infancy or early childhood, pica, rumination disorder; tic disorders, e.g. chronic motor or vocal tic disorder, and Tourette's disorder; other disorders of infancy, childhood, or adolescence, e.g. selective mutism, and stereotypic movement disorder;

delirium, dementia, amnestic and other cognitive disorders, such as Alzheimer's, Creutzfeldt-Jakob disease, dead trauma, Huntington's disease, HIV disease, Pick's disease, and diffuse Lewy body dementia;

conversion hysteria;

conditions connected to normal aging, such as disturbances in motor functions and mental functions;

Parkinson's Disease and related disorders, such as multiple system atrophies, e.g. striatonigral degeneration, olivopontocerebellar atrophy, and shydrager syndrome; progressive supranuclear palsy; corticobasal degeneration; and vascular parkinsonism;

tremors, such as essential, orthostatic, rest, cerebellar, and secondary tremor headaches, such as migraine, cluster headache, tension type headache, and paroxysmal headache;

movement disorders, such as dyskinesias, e.g. in deneral medicine condition, secondary to trauma or vascular insult, hemiballism, athetosis, Sydenham's chorea, and paroxysmal; dystonias; Ekbom's syndrome (restless legs); Wilson's Disease; Hallerworden-Spatz disease;

rehabilitation medicine, e.g. to improve rehabilitation after vascular or traumatic brain injury;

pain in conditions characterized by increased muscular tone, such as fibromyalgia, myofascial syndrome, dystonia, and parkinsonism; as well as conditions related to the above that fall within the larger categories but does not meet the criteria of any specific disorder within those categories.

Synthesis

The synthesis of the present compounds is carried out by methods that are conventional for the synthesis of related known compounds. The syntheses of compounds in Formula 1, in general, comprise the reaction of an intermediate that supplies the alkyl group with an intermediate piperidine or piperazine that supplies the amine group of Formula 2:

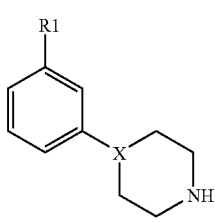

(2)

A convenient method of synthesis of the present compounds is by use of an alkyl iodide (e.g. 1-propyl-iodide). Alternatively, other leaving groups besides iodide may be used on the alkyl group, of course, such as sulfonates, particularly methanesulfonate or toluenesulfonate, bromo and the like. The alkyl intermediate is reacted with the appropriate amine in the presence of any convenient acid scavenger. The usual bases such as alkali metal or alkaline earth metal carbonates, bicarbonates and hydroxides are useful acid scavengers, as are some organic bases such as trialkylamines and trialkanolamines. The reaction medium for such reactions may be any convenient organic solvent which is inert to the basic conditions; acetonitrile, esters such as ethylacetate and the like and halogenated alkane solvents are useful. Usually the reactions will be carried out at elevated temperatures such as from ambient temperature to the reflux temperature of the reaction mixture, particularly from 50° C. to about 100° C.

Another convenient method of synthesis of the present compounds involves reductive amination with an amine of Formula 2:

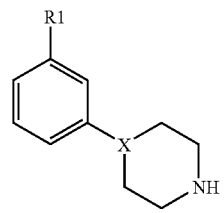

(2)

with an aldehyde or ketone, either in the presence of a reducing agent such as sodium cyanoborohydride or sodium triacetoxyborohydride or followed by reduction, e.g. using catalytic hydrogenation, to give a corresponding compound of Formula 1.

Compounds of Formula 3

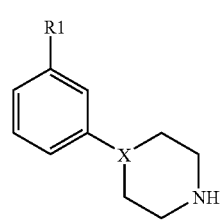

(3)

wherein X=N is accomplished by reacting compounds of Formula 4:

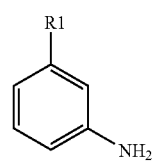

(4)

with compounds of Formula 5:

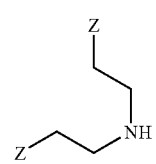

(5)

where Z is a leaving group like iodide. Other leaving groups besides iodide may be used on the alkyl group, of course, such as sulfonates, particularly methanesulfonate or toluenesulfonate, bromo and the like. The alkyl intermediate is reacted with the appropriate amine in the presence of any convenient acid scavenger. The usual bases such as alkali metal or alkaline earth metal carbonates, bicarbonates and hydroxides are useful acid scavengers, as are some organic bases such as trialkylamines and trialkanolamines. The reaction is performed in a suitable solvent such as n-butanol by heating at about 50-150° C.

Compounds of the Formula 1 wherein X=N is also accomplished by reacting compounds of Formula 6:

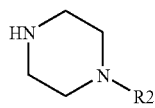
(6)

with an aryl substituted with a leaving group of Formula 7:

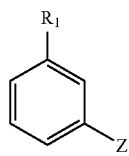
(7)

where Z is halide e.g. chloro, bromo, iodo, or sulfonate e.g. —OSO$_2$CF$_3$, or —OSO$_2$F, in the presence of a base and a zerovalent transition metal catalyst such as Pd or Ni, according to known method (Tetrahedron Letters, vol 37, 1996, 4463-4466, J. Org. Chem., vol. 61, 1996, 1133-1135).

The catalyst, preferably Pd will have the ability to form ligand complex and undergo oxidative addition. Typical Pd catalysts will be Pd$_2$(dba)$_3$ (wherein dba refers to di-benzylidene acetone), Pd(PPh$_3$)$_4$, Pd(OAc)$_2$, or PdCl$_2$[P(o-tol)$_3$]$_2$ and typical phosphine ligands will be BINAP, P(o-tol)$_3$, dppf, or the like. The usual bases such as alkali metal or alkaline earth metal carbonates, bicarbonates and alkyloxides are useful acid scavengers, as are some organic bases such as trialkylamines and trialkanolamines. The reaction medium for such reactions may be any convenient organic solvents, which are inert to the basic conditions; acetonitrile, toluene, dioxane, NMP (N-methyl-2-pyrrolidone), DME (dimethoxyethane), DMF (N,N-dimethylformamide), DMSO (dimethylsulfoxide) and THF (tetrahydrofuran) solvents are useful. Usually the reactions will be carried out at elevated temperatures such as from ambient temperature to the reflux temperature of the reaction mixture, particularly from 50° C. to about 120° C.

Compounds of the Formula 1 wherein X=N is also accomplished by reacting compounds of Formula 6 with an aryl substituted with a leaving group (e.g. F or Cl) via nucleophilic aromatic displacement reactions in the presence of a base as explained above.

Compounds of the Formula 1 wherein X=CH is also accomplished by transition metal catalyzed cross-coupling reaction, known as, for example, Suzuki and Stille reactions, to those skilled in the art.

The reaction may be carried out between compounds of Formula 8:

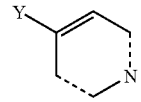
(8)

wherein Y is, for example, a dialkylborane, dialkenylborane or boronic acid (e.g. BEt$_2$, B(OH)$_2$ (dotted lines can be double bonds)) or a trialkyltin (e.g. SnMe$_3$, SnBu$_3$), and an aryl substituted with a leaving group of Formula 7:

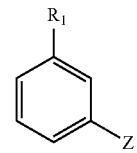
(7)

(for definition of Z, see above) in the presence of a base and a zerovalent transition metal catalyst such as Pd or Ni, according to known methods (Chem. Pharm. Bull., vol 33, 1985, 4755-4763, J. Am. Chem. Soc., vol. 109, 1987, 5478-5486., Tetrahedron Lett., vol. 33, 1992, 2199-2202). In addition, Y can also be a zink- or magnesium-halide group (e.g. ZnCl$_2$, ZnBr$_2$, ZnI$_2$, MgBr$_2$, MgI$_2$) according to known methods (Tetrahedron Lett., vol. 33, 1992, 5373-5374, Tetrahedron Lett., vol. 37, 1996, 5491-5494).

The catalyst, preferably Pd will have the ability to form ligand complex and undergo oxidative addition. The definition of ligands, bases and solvents, is mentioned above.

Alternatively, the transition metal catalyzed cross-coupling reaction can be performed with the opposite substitution pattern:

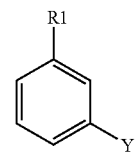
(9)

with an heteroaryl/alkenyl substituted with an leaving group of Formula 10:

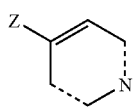
(10)

in the presence of a base and a zerovalent transition metal catalyst such as Pd or Ni, according known methods discussed in the previous paragraph.

Compounds of Formula 11:

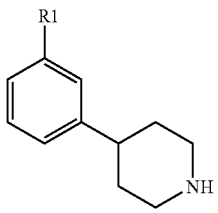

(11)

can be prepared by catalytic hydrogenation of the tetrahydropyridine or pyridine from the previous paragraph, using standard methods known in the art, generally with palladium on carbon, PtO2, or Raney nickel as the catalyst. The reaction is performed in an inert solvent, such as ethanol or ethyl acetate, either with or without a protic acid, such as acetic acid or HCl. When the pyridine ring is quaternized with an alkyl group the ring can be partly reduced by $NaBH_4$ or $NaCNBH_4$, yielding the tetrahydropyridine analog which can further be reduced with catalytic hydrogenation.

Another convenient method of syntheses of compounds of the Formula 1, wherein X=CH is also accomplished by treating arylhalides of Formula 7:

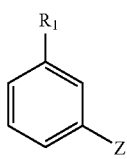

(7)

wherein Z is Cl, Br, or I, with alkyllithium reagents, for example, butyllithium, sec-butyllithium or tertbutyl-lithium, preferably butyllithium or Mg (grignard reaction) in an inert solvent. Suitable solvents include, for example ether or tetrahydrofuran, preferably tetrahydrofuran. Reaction temperatures range from about −110° C. to about 60° C. The intermediate lithium anions or magnesium anions thus formed may then be further reacted with a suitable electrophile of Formula 12:

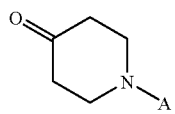

(12)

wherein A is defined as a protecting group like t-Boc (tert-butoxycarbonyl), Fmoc (fluorenylmethoxycarbonyl), Cbz (benzyloxycarbonyl) or a an alkylgroup like benzyl. The intermediates of Formula 13:

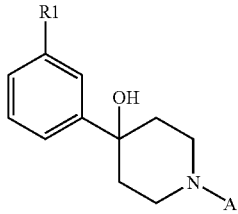

(13)

which are formed require that the hydroxy group be removed so as to result in compounds of Formula 1 (X=CH).

This step may be accomplished by one of several standard methods known in the art. For example, a thiocarbonyl derivative (for example a xanthate) may be prepared and removed by a free radical process, of which are known to those skilled in the art. Alternatively, the hydroxyl group may be removed by reduction with a hydride source such as triethylsilane under acidic conditions, using such as, for example, trifluoroacetic acid or boron trifluoride. The reduction reaction can be performed neat or in a solvent, such as methylene chloride. A further alternative would be to first convert the hydroxyl group to a suitable leaving group, such as tosylate or chloride, using standard methods. The leaving group is then removed with a nucleophilic hydride, such as, for example, lithium aluminium hydride. This last reaction is performed typically in an inert solvent, such as, ether or tetrahydrofuran.

Another alternative method for removing the hydroxyl group is to first dehydrate the alcohol to an olefin with a reagent such as Burgess salt (J. Org. Chem., vol 38, 1973, 26) followed by catalytic hydrogenation of the double bond under standard conditions with a catalyst such as palladium on carbon. The alcohol may also be dehydrated to the olefin by treatment with acid such as p-toluenesulfonic acid or trifluoroacetic acid.

The protecting group, A, is removed under standard conditions known by those skilled in the art. For example, t-Boc cleavages are conveniently carried out with trifluoroacetic acid either neat or in combination with methylene chloride. F-moc is conveniently cleaved off with simple bases such as, ammonia, piperidine, or morpholine, usually in polar solvents such as DMF and acetonitrile. When A is Cbz or benzyl, these are conveniently cleaved off under catalytic hydrogenation conditions. The benzyl group can also be cleaved off under N-dealkylation conditions such as treatment with α-chloroethyl chloroformate (J. Org. Chem., vol 49, 1984, 2081-2082).

It is further possible to convert a radical $R_1$ in a compound of the Formula 1 into another radical $R_1$, e.g. by oxidizing methylsulfide to methylsulfone (for example by m-chloroperoxybenzoic acid), substitution of a triflate or halide group with a cyano group (for example palladium catalyzed cyanation), substitution of triflate or halide group with a ketone (for example palladium catalyzed Heck reaction with butyl vinyl ether), substitution of a triflate or halide group with a carboxamide (for example, palladium catalyzed carbonylation), or cleaving an ether by, for example, converting a methoxy group into the corresponding hydroxyl derivate, which can further be converted into the corresponding mesylate or triflate. The terms mesylate and triflate refers to $OSO_2CH_3$, $CH_3SO_3$ or $OSO_2CF_3$, $CF_3SO_3$, respectively.

In summary, the general process for preparing the present compounds has six main variations, which may briefly be described as follows:

according to Scheme 1:

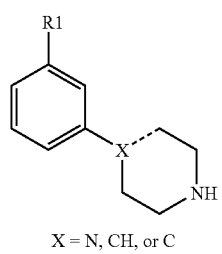

or according to Scheme 2:

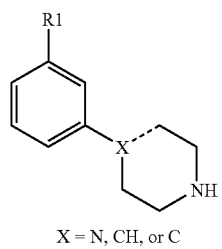

or according to Scheme 3:

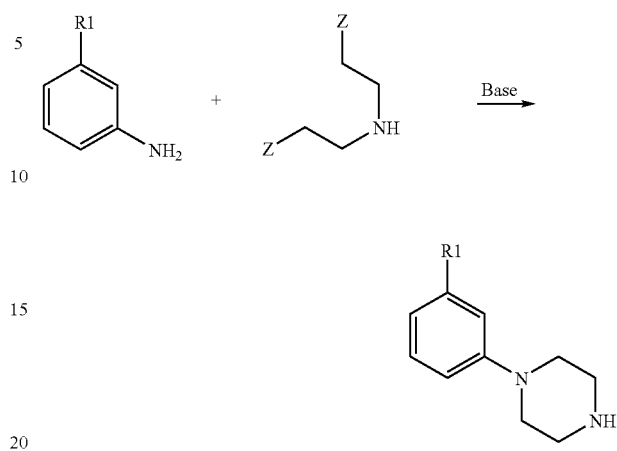

or according to Scheme 4:

or according to Scheme 5:

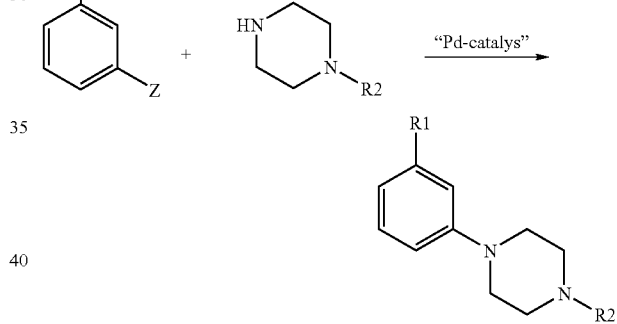

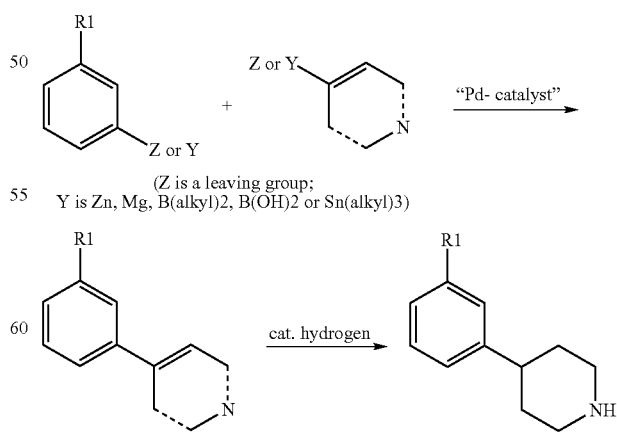

or according to Scheme 6:

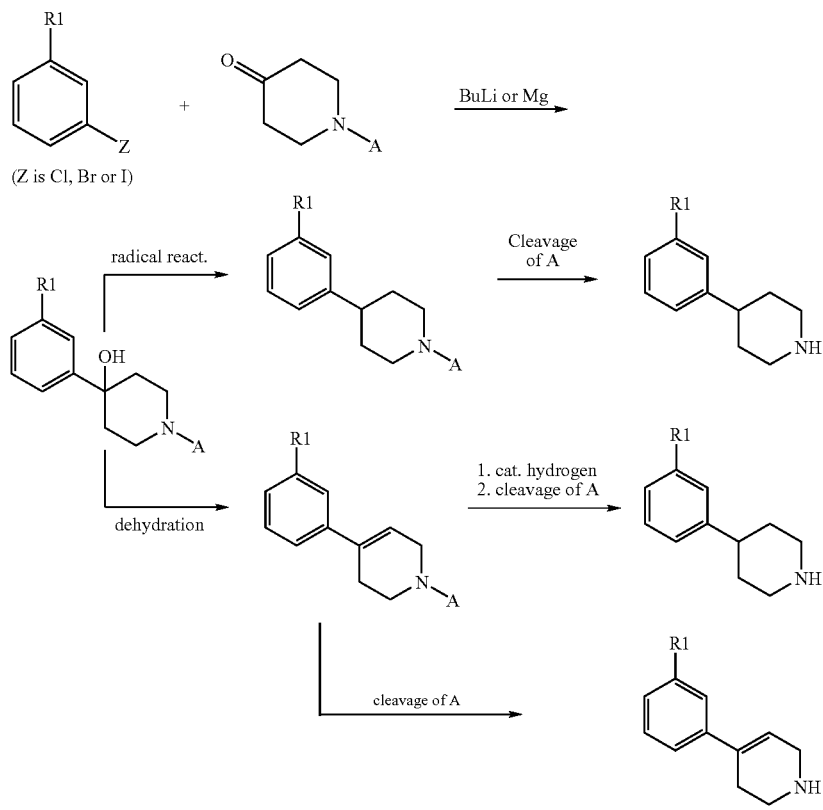

As used herein the term $C_1$-$C_4$ alkyl refers to an alkyl containing 1-4 carbon atoms in any isomeric form. The various carbon moieties are defined as follows: Alkyl refers to an aliphatic hydrocarbon radical and includes branched or unbranched forms such as methyl, ethyl, n-propyl, i-propyl, n-butyl, i-butyl, s-butyl, t-butyl. The term cycloalkyl refers to a radical of a saturated cyclic hydrocarbon such as cyclopropyl, cyclobutyl, cyclopentyl, cyclohexyl.

The term "patient" used herein refers to an individual in need of the treatment according to the invention.

The term "treatment" used herein relates to both treatment in order to cure or alleviate a disease or a condition, and to treatment in order to prevent the development of a disease or a condition. The treatment may either be performed in an acute or in a chronic way.

Both organic and inorganic acids can be employed to form non-toxic pharmaceutically acceptable acid addition salts of the compounds according to the invention. Illustrative acids are sulfuric, nitric, phosphoric, hydrochloric, citric, acetic, lactic, tartaric, palmoic, ethane disulfonic, sulfamic, succinic, cyclohexylsulfamic, fumaric, maleic, and benzoic acid. These salts are readily prepared by methods known in the art.

The pharmaceutical composition containing a compound according to the invention may also comprise substances used to facilitate the production of the pharmaceutical preparation or the administration of the preparations. Such substances are well known to people skilled in the art and may for example be pharmaceutically acceptable adjuvants, carriers and preservatives.

In clinical practice the compounds used according to the present invention will normally be administered orally, rec-tally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidine, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine-capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated in the clinic would be readily apparent to an ordinary skill in the art.

In therapeutical treatment an effective amount or a therapeutic amount of the compounds according to the invention are from about 0.01 to about 500 mg/kg body weight daily, preferably 0.1-10 mg/kg body weight daily.

The compounds may be administered in any suitable way, such as orally or parenterally. The daily dose will preferably be administered in individual dosages 1 to 4 times daily.

It is known for those skilled in the art that replacing a hydrogen in a non-substituted position in the aromatic ring with a fluorine atom may block the possibility for enzymatic hydroxylation which render the compound low oral bioavailability. This type of exchange (H to F) seldom changes the pharmacological profile. Thus, it may be important, in some cases to introduce a fluorine atom in any non-substituted positions in the aromatic ring of compounds of Formula 1 to improve the oral bioavailability.

The invention is further illustrated in the examples below, which in no way are intended to limit the scope of the invention.

EXAMPLE 1

1-(3-Methanesulfonyl-phenyl)-4-propylpiperazine

A suspension of 1-(3-methanesulfonyl-phenyl)piperazine (350 mg) and ground $K_2CO_3$ (403 mg) was stirred in $CH_3CN$ (25 mL) at room temperature. 1-Iodo-propane (712 µL) was added. The mixture was refluxed overnight. The reaction mixture was filtered and the volatiles were evaporated in vacuum. The oily residue was chromatographed on a silica column with $MeOH:CH_2Cl_2$ (1:30 (v/v)) as eluent. Collection of the fractions containing pure product and evaporation of the solvent afforded pure 1-(3-methanesulfonyl-phenyl)-4-propyl-piperazine (220 mg). The amine was converted into the HCl salt and recrystallized from ethanol/diethylether: m.p. 233° C. MS m/z (relative intensity, 70 eV) 282 (M+, 30), 254 (15), 253 (bp), 210 (17), 70 (21).

The following compounds according to Examples 2-11 were prepared in a manner similar to the one described in Example 1.

EXAMPLE 2

1-Propyl-4-(3-Trifluoromethanesulfonyl-phenyl)-piperazine

MS m/z (relative intensity, 70 eV) 336 (M+, 16), 307 (bp), 77 (18), 70 (38), 56 (23).

EXAMPLE 3

1-[3-(4-Propyl-piperazin-1-yl)-phenyl]-ethanone

Beginning with 1-(3-piperazin-1-yl-phenyl)-ethanone and n-Pr-I: m.p. 119° C. (oxalate), MS m/z (rel. intensity, 70 eV) 246 (M+, 10), 217 (33), 132 (18), 70 (bp), 56 (41); Rf 0.23 (EtOAc).

EXAMPLE 4

1-Propyl-4-(3-trifluoromethyl-phenyl)-piperidine

Beginning with 4-(3-Trifluoromethyl-phenyl)piperidine and n-Pr-I: m.p. 195° C. (HCl), MS m/z (rel. intensity, 70 eV) 271 (M+, 4), 243 (16), 242 (bp), 159 (13), 70 (49).

EXAMPLE 5

1-Butyl-4-(3-trifluoromethyl-phenyl)piperidine

Beginning with 4-(3-Trifluoromethyl-phenyl)piperidine and n-Bu-Br: m.p. 222° C. (HCl), MS m/z (rel. intensity, 70 eV) 285 (M+, 3), 243 (12), 242 (bp), 70 (51), 56 (17).

EXAMPLE 6

4-(3-Methanesulfonyl-phenyl)-1-propyl-piperidine m.p. 200° C. (HCl) MS m/z (relative intensity, 70 eV) 281 (M+, 5), 252 (bp), 129 (20), 115 (20), 70 (25.

EXAMPLE 7

4-(3-Methanesulfonyl-phenyl)-1-propyl-1,2,3,6-tetrahydro-pyridine

Beginning with 4-(3-methanesulfonyl-phenyl)-1,2,3,6-tetrahydro-pyridine and iodopropane: MS m/z (relative intensity, 70 eV) 279 (M+, 26), 250 (bp), 171 (6), 128 (12), 115 (8).

EXAMPLE 8

4-(3-Methanesulfonyl-phenyl)-1-ethyl-piperidine

Beginning with 4-(3-methanesulfonyl-phenyl)piperidine and iodoethane: m.p. 158° C. (HCl). MS m/z (rel. intensity, 70 eV) 267 (M+, 20), 252 (bp), 130 (10), 115 (12), 84 (20);

EXAMPLE 9

1-Isopropyl-4-(3-methanesulfonyl-phenyl)-piperidine

Beginning with 4-(3-methanesulfonyl-phenyl)piperidine and i-propylbromide: m.p. 220° C. (HCl); MS m/z (rel. intensity, 70 eV) 281 (M+, 4), 266 (bp), 187 (5), 129 (5), 115 (5)

EXAMPLE 10

4-(3-Methanesulfonyl-phenyl)-1-butyl-piperidine

Beginning with 4-(3-methanesulfonyl-phenyl)piperidine and n-BuCl. MS m/z (rel. intensity, 70 eV) 295 (M+, 3), 252 (bp), 130 (5), 115 (3), 70 (8).

EXAMPLE 11

1-Isobutyl-4-(3-methanesulfonyl-phenyl)-piperidine

Beginning with 4-(3-methanesulfonyl-phenyl)piperidine and i-butylbromide; m.p. 212° C. (HCl); MS m/z (rel. intensity, 70 eV) 295 (M+, 1), 252 (80), 129 (40), 115 (50), 70 (bp)

EXAMPLE 12

3-(1-Propyl-piperidin-4-yl)-benzonitrile

A solution of 3-(1-propyl-piperidin-4-yl)-benzamide (350 mg) and $POCl_3$ (326 μL) in dry DMF (6 ml) was heated at 80° C. for 3 h under an argon atmosphere. Evaporation of the solvent yielded a dark, oily residue, which was dissolved in water. The solution was basified and extracted with $CH_2Cl_2$. The combined organic phases were dried ($MgSO_4$), filtered and evaporated. The oily residue was chromathographed on a silica column with $MeOH:CH_2Cl_2$ (1:19 (v/v)) as eluent. Collection of the fractions containing pure product and evaporation of the solvent afforded pure 3-(1-Propyl-piperidin-4-yl)-benzonitrile (127 mg). The amine was converted into the fumarate salt and recrystallized from ethanol/diethylether: m.p. 122° C.; MS m/z (relative intensity, 70 eV) 228 (M+, 2), 199 (42), 129 (26), 70 (bp) 56 (53).

EXAMPLE 13

1-sec-Butyl-4-(3-methanesulfonyl-phenyl)-piperidine 4-(3-methanesulfonyl-phenyl)-piperidine hydrochloride (20 mg), glacial acetic acid (4.4 mg) and 2-butanone (5.1 mg) were mixed in 1,2-dichloroethane (5 mL). Sodium triacetoxyborohydride (23.5 mg) was added to the solution and the reaction mixture was stirred at room temperature under a nitrogen atmosphere for 5 h (G.L.C. analysis indicated a complete reaction). The reaction was quenched with saturated aqueous $NaHCO_3$ and the product was extracted with $CH_2Cl_2$. The combined organic phases were dried ($MgSO_4$), filtered, and the solvent was evaporated to afford 1-sec-butyl-4-(3-methanesulfonyl-phenyl)piperidine as an oily residue. The product was chromatographed on a silica column with $CH_2Cl_2:MeOH$ (9:1 (v/v)) as eluent. Collection of the fractions containing pure product and evaporation of the solvent afforded pure amine (15 mg, 71%); MS m/z (relative intensity, 70 eV) 295 (M+, 1), 280 (7), 266 (bp), 187 (4), 129 (4).

EXAMPLE 14

Methanesulfonic acid 3-(1-propyl-piperidin-4-yl)-phenyl ester

A solution of 3-(1-propyl-piperidin-4-yl)-phenol (340 mg) and triethylamine (187 mg) in 20 ml of $CH_2Cl_2$ was cooled to 0° C. Then methanesulfonyl chloride (194 mg) dissolved in 10 ml of $CH_2Cl_2$ was added dropwise. The reaction mixture was allowed to reach room temperature and then stirred for 2.5 h at 25° C. The reaction was finally quenched with water. The organic layer was separated and washed with 10% HCl and then 10% $Na_2CO_3$.

After drying ($MgSO_4$) the solvent was removed under reduced pressure. The residue was chromathographed on a silica column using $MeOH:CH_2Cl_2$ (1:9 (v/v)) as eluent. The fractions containing pure methanesulfonic acid 3-(1-propyl-piperidin-4-yl)-phenyl ester were collected, and the solvent was removed in vacuum, affording 206 mg of the title compound. (MS m/z (rel. intensity, 70 eV) 297 (M+, 3), 268 (bp), 189 (24), 131 (13), 79 (16);

The following compounds in Examples 15-19 were prepared in a manner similar to the one described in Example 14.

EXAMPLE 15

Methanesulfonic acid 3-(1-ethyl-piperidin-4-yl)-phenyl ester

Beginning with 3-(1-ethyl-piperidin-4-yl)-phenol and methanesulfonyl chloride. MS m/z (rel. intensity, 70 eV) 283 (M+, 6), 268 (bp), 189 (54), 131 (20), 79 (70);

EXAMPLE 16

Methanesulfonic acid 3-(1-butyl-piperidin-4-yl)-phenyl ester

Beginning with 3-(1-butyl-piperidin-4-yl)-phenol and methanesulfonyl chloride. MS m/z (rel. intensity, 70 eV) 311 (M+, 3), 268 (bp), 189 (20), 131 (18), 79 (12);

EXAMPLE 17

Methanesulfonic acid 3-(4-propyl-piperazin-1-yl)-phenyl ester

Beginning with 3-(4-propyl-piperazin-1-yl)-phenol and methanesulfonyl chloride: m.p 143-144° C. (fumarate); MS m/z (rel. intensity, 70 eV) 298 (M+, 35), 269 (95), 121 (25), 84 (30), 70 (bp);

EXAMPLE 18

Trifluoro-methanesulfonic acid 3-(1-propyl-piperidin-4-yl)-phenyl ester

Beginning with 3-(1-propyl-piperidin-4-yl)-phenol and triflic anhydride MS m/z (rel. intensity, 70 eV) 351 (M+, 4), 322 (65), 189 (30), 131 (20), 69 (bp).

EXAMPLE 19

Trifluoro-methanesulfonic acid 3-(1-ethyl-piperidin-4-yl)-phenyl ester

Beginning with 3-(1-ethyl-piperidin-4-yl)-phenol and triflic anhydride: MS m/z (rel. intensity, 70 eV) 337 (M+, 4), 322 (65), 189 (30), 131 (20), 69 (bp).

EXAMPLE 20

1-[3-(1-Propyl-piperidin-4-yl)-phenyl]-ethanone

To a stirred solution of trifluoro-methanesulfonic acid 3-(1-propyl-piperidin-4-yl)-phenyl ester (300 mg) in DMF (4 ml) under argon atm at r.t. was subsequently added $NEt_3$ (356 μL), butyl vinyl ether (823 μL), 1,3-bis(diphenylphosphino) propane (50 mg), and $Pd(OAc)_2$ (19 mg). The reaction mixture was then heated to 80° C. and after 2 h the reaction was stopped. 5% Hydrochloric acid solution (6 ml) was added and the combined mixture stirred for 45 min. Then $CH_2Cl_2$ was added and the phases were separated. The aqueous layer was then extracted with $CH_2Cl_2$. The combined organic phases were dried ($MgSO_4$), filtered and evaporated to dryness. The crude product was purified by flash chromatography (MeOH:$CH_2Cl_2$ (1:9 (v/v)). Collection of the fractions containing pure product and evaporation of the solvent afforded pure 1-[3-(1-Propyl-piperidin-4-yl)-phenyl]-ethanone (35 mg). MS m/z (rel. intensity, 70 eV) 245 (M+, 4), 216 (bp), 100 (19), 70 (36), 57 (13).

EXAMPLE 21

1-Propyl-4-(3-trifluoromethylsulfonylphenyl)-1,2,3,6-tetrahydropyridine 4-(3-Trifluoromethylsulfonylphenyl)-Pyridine (0.3 g) was dissolved in 1-iodo-propane (2 ml) and heated to 100° C. for 2 h. Then the voilatiles were evaporated and the residue redissolved in abs EtOH (20 ml) and $NaBH_4$ (340 mg) was added portions wise at −20° C. The mixture was then allowed to reach r.t. and stirred over night. To the mixture was added 10% $Na_2CO_3$ solution (20 ml). The aqueous layer was extracted with $CH_2Cl_2$ and the combined organic phases were dried ($MgSO_4$), filtered and evaporated to dryness. The crude product was purified by flash chromatography (MeOH:$CH_2Cl_2$ (1:9 (v/v)). Collection of the fractions containing pure product and evaporation of the solvent afforded pure 1-propyl-4-(3-trifluoromethylsulfonylphenyl)-1,2,3,6-tetrahydropyridine (150 mg). MS m/z (rel. intensity, 70 eV) 333 (M+, 21), 305 (16), 304 (bp), 171 (14), 128 (14). Rf 0.55 (MeOH)

EXAMPLE 22

1-Propyl-4(3-trifluoromethylsulfonylphenyl)-piperidine

Beginning with 1-propyl-4-(3-trifluoromethylsulfonyl-phenyl)-1,2,3,6-tetrahydropyridine, 1-Propyl-4-(3-trifluoromethylsulfonylphenyl)-piperidine was recovered by the procedure described in Preparation 9. MS m/z (relative intensity, 70 eV) 335 (M+, 3), 307 (17), 306 (bp), 173 (26), 70 (10).

EXAMPLE 23

1-Allyl-4-(3-methanesulfonyl-phenyl)-piperidine

Beginning with 4-(3-methanesulfonyl-phenyl)piperidine and allylbromide, the titled compound was recovered by the procedure described in Example 1. MS m/z (relative intensity, 70 eV) 279 (M+, 74), 96 (bp), 82 (98), 68 (74), 55 (93). Rf=0.42 (MeOH, 0.08 (EtOAc).

EXAMPLE 24

4-(3-Methanesulfonyl-phenyl)-1-(tetrahydrofuran-2-ylmethyl)-piperidine

Beginning with 4-(3-methanesulfonyl-phenyl)piperidine and tetrahydrofurfuryl chloride, the titled compound was recovered by the procedure described in Example 1. MS m/z (relative intensity, 70 eV) 323 (M+, 1), 252 (bp), 129 (9), 115 (6), 70 (17). Rf=0.3 (MeOH, 0.03 (EtOAc).

Syntheses of intermediates used in the above Examples are described in the preparations below.

Preparation 1: 4-Hydroxy-4-(3-methylsulfanyl-phenyl)piperidin-1-carboxylic acid tert-butyl ester 1-Bromo-3-methylsulfanyl-benzene (5.0 g, 24.6 mmol) was dissolved in dry THF (40 ml) and cooled to −78° C. under a stream of Argon (g). n-BuLi (12.8 ml, 2.5 M in hexane, 31.9 mmol) was added dropwise via syringe and the reaction mixture was stirred for an additional 30 min at −78° C., then the temperature was increased to 0° C. for 5 min and then decreased to −78° C. 1-tert-Butoxycarbonyl-4-piperidone (5.4 g, 27.06 mmol) dissolved in dry THF (30 ml) was added via syringe. The reaction mixture was allowed to reach room temperature and then stirred for 1 hour, and finally quenched with saturated ammonium chloride solution (30 ml). The mixture was extracted several times with EtOAc and the combined organic phases were dried ($MgSO_4$), filtered and evaporated to dryness. The oily residue was chromathographed on a silica column using $CH_2Cl_2$:MeOH (19:1 (v/v)) as eluent, yielded 4-hydroxy-4-(3-methylsulfanyl-phenyl)-piperidin-1-carboxylic acid tert-butyl ester (6 g, 76%). MS m/z (relative intensity, 70-eV) 323.1 (M+, 6), 223.0 (11), 178.0 (7), 152 (3), 57.0 (bp), 56 (30).

Preparation 2: 1-Benzyl-4-(3-methoxy-phenyl)-piperidin-4-ol

Beginning with 3-bromoanisole (5 g) and 1-benzyl-4-piperidone (5.5 g), 4.58 g of 1-benzyl-4-(3-methoxyphenyl)-piperidin-4-ol was recovered by the procedure described in Preparation 1. MS m/z (relative intensity, 70 eV) 297 (M+, 8), 279 (13), 206 (28), 146 (17), 91 (bp).

Preparation 3: 1-Benzyl-4-(3-trifluoromethyl-phenyl)-piperidin-4-ol

Beginning with 3-trifluoromethyl-iodobenzene (3 g) and 1-benzyl-4-piperidone (2.1 g), 1.75 g of the title compound was recovered by the procedure described in preparation 1. MS m/z (rel. intensity, 70 eV) 335 (M+, 29), 244 (22), 146 (19), 91 (bp), 56 (19).

Preparation 4: 4-(3-Methylsulfanyl-phenyl)-1,2,3,6-tetrahydro-pyridine

4-Hydroxy-4-(3-methylsulfanyl-phenyl)-piperidin-1-carboxylic acid tert-butyl ester (3.97 g) was dissolved in $CH_2Cl_2$ (500 ml) and trifluoroacetic acid (80 ml) was added in one portion. The mixture was refluxed for one hour and then washed with two portions of 10%-$Na_2CO_3$, dried ($MgSO_4$), filtered and evaporated to dryness. Yield 2.07 g. MS m/z (relative intensity, 70 eV) 205 (M+, 73), 158 (44), 129 (95), 128 (80), 82 (bp).

Preparation 5: 1-Benzyl-4-(3-methoxy-phenyl)-1,2,3,6-tetrahydro-pyridine

Beginning with 1-Benzyl-4-(3-methoxy-phenyl)piperidin-4-ol (4.5 g) and trifluoroacetic acid (80 ml), 3.5 g of 1-benzyl-4-(3-methoxy-phenyl)-1,2,3,6-tetrahydro-pyridine was recovered by the procedure described in Preparation 4. MS m/z (relative intensity, 70 eV) 279 (M+, 35), 145 (13), 115 (15), 91 (bp), 65 (22).

Preparation 6: 1-Benzyl-4-(3-trifluoromethyl-phenyl)-1,2,3,6-tetrahydro-pyridine Beginning with 1-Benzyl-4-(3-trifluoromethylphenyl)-piperidin-4-ol (1.74 g), 1.44 g of the title compound was recovered by the procedure described in preparation 4 (neat $CF_3COOH$). MS m/z (rel. intensity, 70 eV) 317 (M+, 71), 226 (13), 172 (15), 91 (bp), 65 (17).

Preparation 7: 4-(3-Methylsulfanyl-phenyl)-3,6-dihydro-2H-pyridine-1-carboxylic acid methyl ester 4-(3-Methylsulfanyl-phenyl)-1,2,3,6-tetrahydropyridine (2 g) and NEt3 (1 g) were dissolved in $CH_2Cl_2$ (75 ml) and cooled to 0° C. Methyl chloroformate (0.96 g) dissolved in $CH_2Cl_2$ (20 ml) was added dropwise and the reaction mixture was then allowed to reach room temperature. After an additional two hours at room temperature the reaction mixture was washed with 10% $Na_2CO_3$ solution, dried (MgSO4), filtered and concentrated by evaporation. The oily residue was chromatographed on a silica column using $CH_2Cl_2$:MeOH (19:1 (v/v)) as eluent, 4-(3-methylsulfanyl-phenyl)-3,6-dihydro-2H-pyridine-1-carboxylic acid methyl ester (1.4 g). MS m/z (relative intensity, 70 eV) 263 (M+45), 248 (89), 129 (83), 128 (bp), 59 (96).

Preparation 8: 4-(3-Methanesulfonyl-phenyl)-3,6-dihydro-2H-pyridine-1-carboxylic acid methyl ester 4-(3-Methylsulfanyl-phenyl)-3,6-dihydro-2H-pyridine-1-carboxylic acid methyl ester (1.4 g) was dissolved in $CH_2Cl_2$ (150 ml) and cooled to 0° C. m-Chloroperoxybenzoic acid (2.48 g) was added portions wise and the mixture was stirred at room temperature for three hours. The resulting clear solution was washed with 10%-$Na_2CO_3$ solution, dried ($MgSO_4$), filtered and concentrated by evaporation and yielding an oily residue (1.3 g). MS m/z (relative intensity, 70 eV) 295 (M+, 19), 280 (56), 129 (70), 128 (89), 59 (bp).

Preparation 9: 4-(3-Methanesulfonyl-phenyl)-piperidin-1-carboxylic acid methyl ester 4-(3-Methanesulfonyl-phenyl)-3,6-dihydro-2H-pyridine-1-carboxylic acid methyl ester (2.0 g) was dissolved in methanol (40 ml). Concentrated hydrochloric acid (2 ml) and Pd/C (500 mg) were added. The resulting mixture was hydrogenated under a hydrogen gas pressure (50 psi) for 8 h and then filtered through a pad of celite. The solvent was evaporated in vacuum and the residue was purified by flash chromatography ($CH_2Cl_2$:MeOH, 3:1 (v/v)). Yield 0.92 g MS m/z (relative intensity, 70 eV) 297 (M+, 54), 282 (62), 238 (bp), 115 (92), 56 (93).

Preparation 10: 4-(3-Methoxy-phenyl)-piperidine

Beginning with 1-Benzyl-4-(3-methoxy-phenyl)-1,2,3,6-tetrahydro-pyridine (5.1 g) and 900 mg Pd/C, 1.7 g of 4-(3-Methoxy-phenyl)-piperidine was recovered by the procedure described in Preparation 9. The oily residue was purified by flash chromatography ($SiO_2$, $CH_2Cl_2$:MeOH, 3:1 (v/v) with 1% $NEt_3$) to give the pure title compound. MS m/z (relative intensity, 70 eV) 191 (M+, 75), 160 (60), 83 (55), 57 (80), 56 (bp)

Preparation 11: 4-(3-Trifluoromethyl-phenyl)-piperidine

Beginning with 1-Benzyl-4-(3-trifluoromethylphenyl)-1,2,3,6-tetrahydro-pyridine (1.44 g), 1 g of the title compound as HCl salt was recovered by the procedure described in preparation 9. m.p. 202° C. (HCl); MS m/z (rel. intensity, 70 eV) 229 (M+, 44), 228 (33), 83 (12), 57 (54), 56 (bp).

Preparation 12: 4-(3-Methanesulfonyl-phenyl-piperidine 4-(3-Methanesulfonyl-phenyl)-piperidin-1-carboxylic acid methyl ester (0.92 g) dissolved in ethanol (15 ml) and 8 M HCl (40 ml) was refluxed for 12 hours. The mixture was then evaporated in vacuum to dryness. Yield 0.85 g MS m/z (relative intensity, 70 eV) 239 (M+, 59), 238 (50), 69 (20), 57 (79), 56 (bp)

Preparation 13: 3-Piperidin-4-yl-phenol 4-(3-Methoxy-phenyl)-piperidine (1.7 g) was dissolved in 48-% HBr (60 ml) and stirred at 120° C. under an Argon-atmosphere for 3 h. The excess of HBr was then evaporated and absolute ethanol added and evaporated. This procedure was repeated several times to yield dry crystals of 3-piperidin-4-yl-phenol×HBr (2.3 g). MS m/z (relative intensity, 70 eV) 177 (M+, bp), 176 (23), 91 (14), 57 (44), 56 (60).

Preparation 14: 3-(1-Propyl-piperidin-4-yl)-phenol×HBr

Beginning with 3-piperidin-4-yl-phenol×HBr (300 mg) and n-propyl iodide (200 mg), 340 mg of 3-(1-propyl-piperidin-4-yl)-phenol was recovered by the procedure described in Example 1. The HBr salt was prepared to provide the title compound. MS m/z (rel. intensity, 70 eV) 219 (M+, 21), 190 (bp), 119 (22), 91 (30), 70 (63); m.p. 181-184° C. (HBr).

Preparation 15: 3-(1-Ethyl-piperidin-4-yl)-phenol

Beginning with 3-piperidin-4-yl-phenol×HBr (200 mg) and Ethyl iodide (121 mg), 120 mg of 3-(1-ethylpiperidin-4-yl)-phenol was recovered by the procedure described in Example 1. MS m/z (rel. intensity, 70 eV) 205 (M+, 12), 190 (bp), 119 (36), 91 (22), 70 (87).

Preparation 16: 3-(1-Butyl-piperidin-4-yl)-phenol

Beginning with 3-piperidin-4-yl-phenol×HBr (200 mg) and n-butyl chloride (73 mg), 118 mg of 3-(1-butyl-piperidin-4-yl)-phenol was recovered by the procedure described in Example 1. MS m/z (rel. intensity, 70 eV) 233 (M+, 6), 190 (bp), 119 (42), 91 (26), 70 (45).

Preparation 17: 1-(3-Methanesulfonyl-phenyl)-piperazine

A mixture of 1-bromo-3-methanesulfonyl-benzene (0.8 g), piperazine (1 g), sodium tert-butoxide (0.5 g) BINAP (42 mg)

and [Pd$_2$(dba)$_3$ (38 mg) in toluene (7 ml) was heated under argon at 80° C. for 24 h. After cooling to roomtemperature, the solvent was evaporated to dryness. The crude material was purified by flash chromatography on silica gel using EtOAc. Yield 0.48 g: MS m/z (rel. intensity, 70 eV) 240 (M+, 17), 199 (12), 198 (bp), 119 (9), 56 (7).

Preparation 18:
1-(3-Trifluoromethanesulfonyl-phenyl)-piperazine

Beginning with 3-bromo-trifluoromethanesulfonyl-benzene and piperazine, the titled cmp was recovered by the procedure described in Preparation 17. MS m/z (rel. intensity, 70 eV) 294 (M+, 22), 252 (bp), 119 (32), 104 (10), 56 (15). (45).

Preparation 19:
1-(3-Piperazin-1-yl-phenyl)-ethanone

Beginning with 3-bromo-acetophenone and piperazine, the titled cmp was recovered by the procedure described in Preparation 17. MS m/z (rel. intensity, 70 eV) 204 (M+, 5), 162 (35), 77 (30), 57 (35), 56 (bp).

Preparation 20: 3-(1-Propyl-piperidin-4-yl)-benzoic acid methyl ester

A mixture of trifluoro-methanesulfonic acid 3-(1-propyl-piperidin-4-yl)-phenyl ester (1.2 g), triethyl amine (0.9 g), MeOH (5.4 ml), Pd(OAc)$_2$ (25 mg) and 1,3-bis(di-phenyl-phosphino)propane (45 mg) in 15 ml DMSO was stirred at room temperature for 15 min. A stream of CO (g) was passed through the solution for 4-5 min., and then the reaction vessel was placed under a sligthly positive pressure of CO (g). The temp was increased to 70° C. After 6 h the reaction was allowed to cool to r.t. Water was then added, and the aqueous solution was extracted with five portions of ethyl acetate and the combined organic phases were dried (MgSO$_4$), and evaporated. The residue was chromathographed on a silica column using MeOH:CH$_2$Cl$_2$ (1:9 (v/v)) as eluent. The fractions containing pure titled compound were collected, and the solvent was removed in vacuum, affording 650 mg of the titled compound. (MS m/z (rel. intensity, 70 eV) 261 (M+, 5), 233 (16), 232 (bp), 161 (5), 70 (20)

Preparation 21:
3-(1-Propyl-piperidin-4-yl)-benzamide

A solution of 3-(1-Propyl-piperidin-4-yl)-benzoic acid methyl ester (0.6 g) and formamide (320 µL) in DMF (9 ml) was heated to 100° C. under a blanket of argon. Sodium methoxide in methanol (30%, 770 µL) was added dropwise and after 1 h, GC analysis revealed the complete absence of starting material and indicated the titled compound as the sole product. After cooling, CH$_2$Cl$_2$ was added and the resulting solution was filtered through a pad of celite and evaporated to dryness. The residue was chromathographed on a silica column using MeOH:CH$_2$Cl$_2$ (1:3 (v/v)) as eluent. The fractions containing pure titled compound were collected, and the solvent was removed in vacuum, affording 400 mg of the titled compound. m.p. 182° C. (oxalate) (MS m/z (rel. intensity, 70 eV) 246 (M+, 4), 217 (bp), 131 (19), 100 (22), 70 (63).

Preparation 22:
4-(3-Trifluoromethylsulfonyl-phenyl)-pyridine

1-Bromo-3-trifluoromethylsulfonyl benzene (580 mg) and 4-pyridine-boronic acid (275 mg) was dissolved in toluene (5 ml) and abs EtOH (5 ml). To the mixture was then added Na$_2$CO$_3$ (424 mg) and Pd(PPh$_3$)$_4$ (119 mg) under an atmosphere of Argon. The resulting mixture was heated to 90° C. for 18 h. Then CH$_2$Cl$_2$ was added and the organic phase was washed with water and dried (MgSO$_4$), filtered and evaporated to dryness. The residue was then used without any further purification. (MS m/z (rel. intensity, 70 eV) 287 (M+, 33), 218 (22), 154 (bp), 127 (56), 69 (27).

The following tests were used for evaluation of the compounds according to the invention.

In vivo Test: Behavior

For behavioral testing, the animals were placed in separate motility meter boxes 50×50×50 cm equipped with an array of 16×16 photocells (Digiscan activity monitor, RXYZM (16) TAO, Omnitech Electronics, USA), connected to an Omnitech Digiscan analyzer and a Apple Macintosh computer equipped with a digital interface board (NB DIO-24, National Instruments, USA). Behavioral data from each motility meter box, representing the position (center of gravity) of the animal at each time, were recorded at a sampling frequency of 25 Hz and collected using a custom written LABView™ application. The data from each recording session were analyzed with respect to distance traveled and small-scale movements, e.g. stops in the center of the behavior recording arena, during the recording session. To determine stops in the center, velocity at each time point is calculated as the distance traveled since the preceding sample divided by the time elapsed since the preceding sample. The number of stops is then calculated as the number of times that the velocity changes from a non-zero value to zero. The number of stops in the center of the behavioral recording arena is calculated as the number of stops occurring at a position at least ten centimeters from the edges of the recording arena. For behavioral testing of habituated rats, the animals were placed in the motility meter boxes 30 minutes before the administration of test compound. Each behavioral recording session lasted 60 or 30 minutes, starting immediately after the injection of test compound. Similar behavioral recording procedures was applied for non-habituated rats, habituated rats and drug pre-treated rats. Rats pre-treated with d-amphetamine are given the dose 1,5 mg/kg s.c. 5 min before the behavioral session in the motility meter. Rats pre-treated with dizolcipine (Mk-801) are given the dose 0,7 mg/kg i.p. 90 min before the behavioral session in the motility meter.

In vivo Test: Neurochemistry

After the behavioral activity sessions the rats were decapitated and their brains rapidly taken out and put on an ice-cold petri-dish. The limbic forebrain, the striatum, the frontal cortex and the remaining hemispheral parts of each rat were dissected and frozen. Each brain part was subsequently analyzed with respect to its content of monoamines and their metabolites. The monoaminergic indices analyzed were dopamine (DA), 3,4-dihydroxyphenylacetic acid (DOPAC), homovanillic acid (HVA), 3-methoxytyramine (3-MT), serotonin (5-HT), 5-hydroxyindole acetic acid (5-HVA), and noradrenaline (NA). All monoaminergic indices in the dissected tissue were analyzed by means of HPLC with electrochemical detection as described by Svensson K, et al., 1986, Naunynschmiedeberg's Arch Pharmacol 334: 234-245 and references cited therein.

In vivo Test: Pharmacokinetics in the Rat

To determine oral availability (F) and plasma half life (t1/2) of test compounds according to the invention experiments performed in the rat were undertaken. On day one rats were implanted with one catheter in the jugular vein and one catheter in the carotid artery under ketamine anesthesia. On day three test compound is injected either orally or in the jugular vein catheter. Blood samples are collected during 8 hours from the arterial catheter. The blood samples were heparinized and centrifuged. Plasma is collected from the centrifuged samples and frozen. The levels of test compound were subsequently determined in each sample by means of gas chromatography-mass spectrometry (Hewlett-Packard 5972MSD). The plasma samples, taken from the rats of the Sprague-Dawley strain, (0.5 ml) were diluted with water (0.5 ml), and 30 pmol (50 µl) of ((−)-S-3-(3-Ethylsulfonylphenyl)-N-n-propyl-piperidine as internal standard was added. The pH was adjusted to 11.0 by the addition of 25 µl saturated $Na_2CO_3$. After mixing, the samples were extracted with 4 ml dichloromethane by shaking for 20 min. The organic layer was, after centrifugation, transferred to a smaller tube and evaporated to dryness under a stream of nitrogen and subsequently redissolved in 40 µl toluene for GC-MS analysis. A standard curve over the range of 1-500 pmol was prepared by adding appropriate amounts of test compound to blank plasma samples. GC was performed on a HP-Ultra 2 capillary column (12 m×0.2 mm ID), and 2 µl was injected in the splitless mode. The GC temperature was held at 90° C. for 1 minute following injection, and was then increased by 30° C./min to the final temperature of 290° C. Each sample was run in duplicate. The lowest detectable concentration of test compound was generally found to be 1 pmol/ml.

The invention claimed is:

1. A 3-substituted 4-(phenyl-N-alkyl)-piperazine compound of Formula 1:

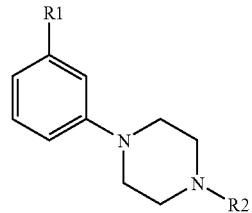

wherein:
$R_1$ is selected from the group consisting of $OSO_2CF_3$, $OSO_2CH_3$, $SO_2R_3$, $COCF_3$, $COCH_3$ and $COCH_2CH_3$, wherein $R_3$ is as defined below;
$R_2$ is selected from the group consisting of $C_1$-$C_4$ alkyls, allyl, $CH_2CH_2CH_2F$, $CH_2CF_3$, 3,3,3-trifluoropropyl and 4,4,4-trifluorobutyl;
$R_3$ is selected from the group consisting of $C_1$-$C_3$ alkyls, $CF_3$, and $N(CH_3)_2$;
with the proviso that when $R_1$ is $SO_2R_3$ and $R_3$ is a $C_1$-$C_3$ alkyl, then $R_2$ is not $CH_2CH_2OCH_3$;
or a pharmaceutically acceptable salt thereof.

2. A compound according to claim 1, wherein $R_1$ is selected from the group consisting of $OSO_2CF_3$, $OSO_2CH_3$, $SO_2CH_3$, $SO_2CF_3$, $COCH_3$ and $SO_2N(CH_3)_2$.

3. A compound according to claim 1, wherein $R_2$ is selected from the group consisting of n-propyl and ethyl.

4. A pharmaceutical composition comprising a compound according claim 1 and one or more pharmaceutically acceptable carriers or diluents.

5. A pharmaceutical composition according to claim 4, formulated for oral administration.

6. A pharmaceutical composition according to claim 5, formulated as a tablet.

7. A pharmaceutical composition according to claim 5, formulated as a capsule.

8. A pharmaceutical composition according to claim 4, formulated for administration by injection.

* * * * *